United States Patent [19]

Chimenti et al.

[11] Patent Number: 5,424,542

[45] Date of Patent: Jun. 13, 1995

[54] METHOD TO OPTIMIZE PROCESS TO REMOVE NORMAL PARAFFINS FROM KEROSINE

[75] Inventors: Robert J. L. Chimenti, Short Hills; Gerald M. Halpern, Bridgewater, both of N.J.

[73] Assignee: Exxon Research and Engineering Company, Florham Park, N.J.

[21] Appl. No.: 125,061

[22] Filed: Sep. 21, 1993

[51] Int. Cl.6 .................. G01N 21/00; G01N 21/35
[52] U.S. Cl. .................. 250/339.12; 250/343; 356/436
[58] Field of Search .............. 250/339, 339.12, 343, 250/341, 339.01, 339.06, 340, 573, 341.1, 340; 356/436

[56] References Cited

U.S. PATENT DOCUMENTS

| | | | |
|---|---|---|---|
| 5,082,985 | 1/1992 | Crouzet et al. | 585/501 |
| 5,121,986 | 6/1992 | Rutz | 356/133 |
| 5,145,785 | 9/1992 | Maggard et al. | 250/339 X |
| 5,223,714 | 6/1993 | Maggard | 250/343 |

FOREIGN PATENT DOCUMENTS 9115762 10/1991 WIPO ............. 250/339.12

OTHER PUBLICATIONS

Evans et al., 'Determination of Carbon-Hydrogen Groups in High Molecular Weight Hydrocarbons', Anal. Chem., vol. 23, No. 11, 1951 pp. 1604–1610.

Primary Examiner—Constantine Hannaher
Assistant Examiner—Edward J. Glick
Attorney, Agent, or Firm—Ronald D. Hantman

[57] ABSTRACT

A method uses near-infrared radiation to optimize the removal or separation of normal paraffins from a kerosene feed stream. The absorptivity of a feed stream and/or sievate is determined for at least one near-infrared wavelength. The weight percent of the normal paraffins in the feed stream and/or sievate is determined from the absorptivity. The determined weight percent is used to control the removal or separation of normal paraffins from the kerosene feed stream.

17 Claims, 5 Drawing Sheets

METHOD TO OPTIMIZE PROCESS TO REMOVE NORMAL PARAFFINS FROM KEROSINE

BACKGROUND OF THE INVENTION

The invention relates to optimizing a process to remove normal paraffins from a feedstream. In particular, the present invention relates to optimizing a process based upon the determination of the normal paraffin content of kerosene.

Petroleum distillates in the kerosene boiling range may contain up to 30 weight percent (wt %) normal paraffins. In order to meet product quality specifications for refined kerosene, the normal paraffin content must be reduced to below 5 wt %. The normal paraffins which are removed are fractionated and sold as additional products.

Normal paraffins may be removed from kerosene by selective absorbers, such as certain zeolite molecular sieves, or membranes. In a zeolite separation process, pairs of fixed beds containing these zeolites are used in commercial processes, to continuously remove the normal paraffins from kerosene feeds. In this process, for example, the feed is vaporized and introduced into one of the beds. As the kerosene vapor front propagates through the bed, normal paraffins are selectively retained in the pore structure of the molecular sieves. The material which emerges from the bed, often called the "sievate", is depleted in normal paraffins. As used herein, sievate means the product of a separator which includes all of the feed components, other than the separated normal paraffins. The material retained in the bed, called the "desorbate", is comprised almost entirely of the normal paraffins which have been removed from the kerosene.

When the bed becomes nearly saturated with normal paraffins, the feed is switched to the second bed. While the second bed absorbs the normal paraffins from the kerosene, the paraffins that are retained in the first bed are desorbed by ammonia vapor, as an example, and subsequently recovered for further processing. The cycle time is approximately six minutes in commercial-scale processes.

Variation in the normal paraffin content of kerosene feedstocks, the lack of an infinitely sharp kerosene vapor front, and the lack of complete absorption selectivity by the molecular sieves are factors which contribute to a variation in the optimum time at which the feed should be switched between beds.

There are economic benefits to switching the feed between beds at the optimum time in the absorption process. Reduced through-put and higher energy costs for inefficient desorption result if the switching time is shorter than optimum. Contamination of the sievate stream by normal paraffins occurs, if the switching time exceeds the optimum. Product quality is reduced and excessive costs may result from storage of off-spec product and, possibly, from reprocessing.

The optimum switching time may be determined in two ways. Measurement of the normal paraffin content of the feed can be used with an accurate process model to compute the optimum time for the particular feed and process conditions. Alternatively, the normal paraffin build-up in the sievate can be monitored to determine the time to switch beds before contamination of the sievate occurs. Both control strategies require a rapid, accurate, and precise on-line determination of the normal paraffin content of the kerosene feed or sievate.

Gas chromatography (GC) is the method currently used to determine the normal paraffin content of kerosene. The method has poor reproducibility due to thermal decomposition of the paraffins on the chromatographic column upon thermal desorption. The repeatability of the method is approximately 3 wt %. In addition, the measurement time is about 20 minutes and, therefore, exceeds the 6 minute process cycle time. The present invention is based upon absorption of light which overcomes the limitations of the GC technique.

SUMMARY OF THE INVENTION

The present invention includes a method to determine the normal paraffin content of a petroleum distillate. This allows a process for separating normal paraffins from petroleum distillates to be optimized in order to maximize the separation. The method includes the steps of irradiating a hydrocarbon feed stream, such as a petroleum distillate, containing normal paraffins with near-infrared radiation, determining the absorptivity of the hydrocarbon feed stream at, at least, one selected wavelength, and determining the weight percent of the paraffin content from the optical absorptivity.

In a preferred embodiment, the difference between the absorptivity at two wavelengths is used in order to minimize possible instrument errors.

In another preferred embodiment, the petroleum distillate is kerosene and the two selected wavelengths selected from one of two wavelength regions, are at about 1210 nm and 1196 nm or about 927 nm and 916 nm.

DESCRIPTION OF THE PREFERRED EMBODIMENT

Figure 1:
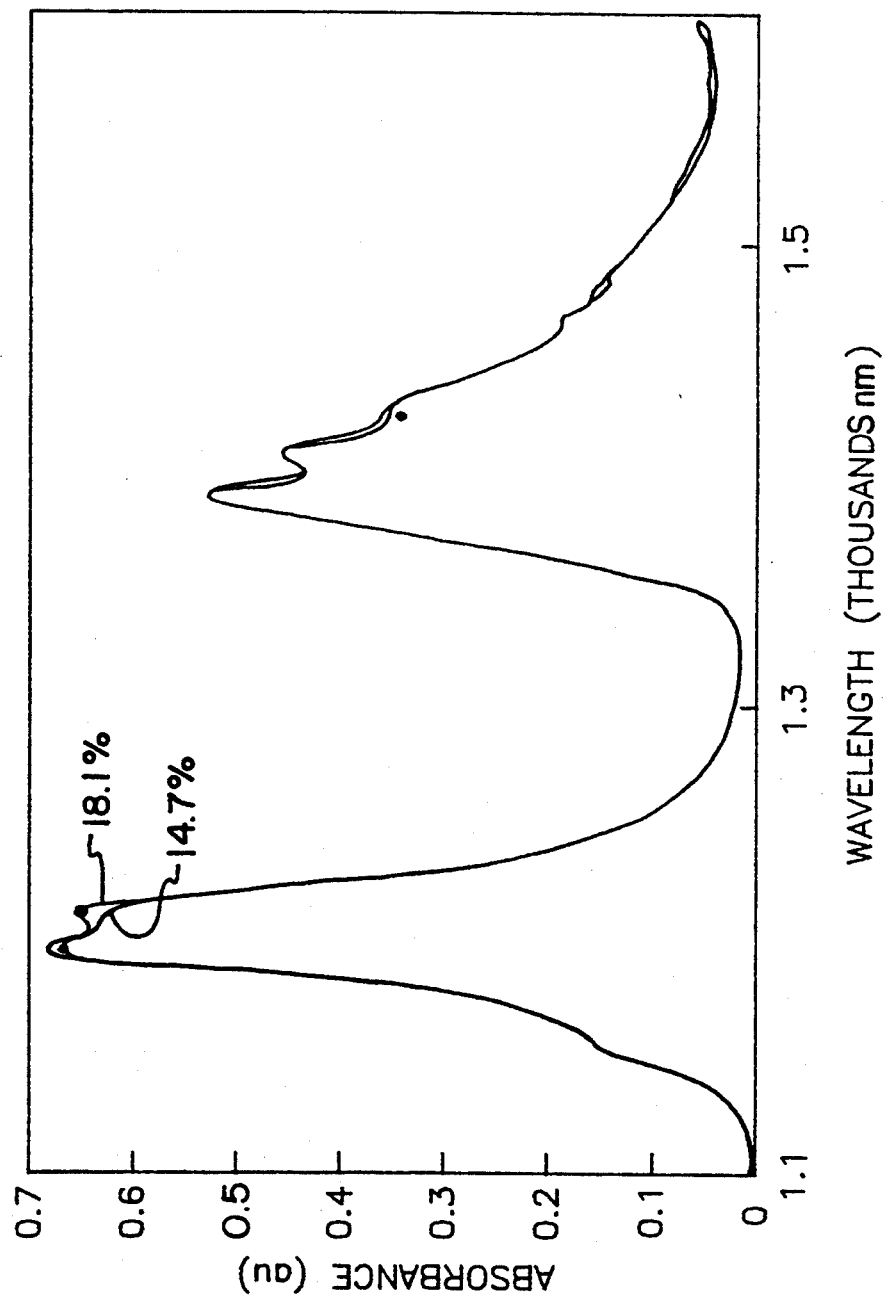
FIG. 1 shows the absorption spectra taken in a 1 cm path-length cell for two kerosene feed samples having normal paraffin content of 14.7 wt % and 18.1 wt % as determined by gas chromatgraphy.

All hydrocarbon molecules absorb light whose energy corresponds to a vibrational frequency of the oscillatory stretching motions of their carbon-hydrogen bonds. In the present invention, hydrocarbons, which are petroleum distillates and which boil in the kerosene boiling range, absorb light between 1100 nm and 1300 nm and between 850 nm and 1000 nm, and more specifically, at 1210 nm and 927 nm and at 1196 nm and 916 nm. Absorption at 1210 nm and 927 nm mainly correspond to the carbon-hydrogen vibrational motion of the $CH_2$ groups, while absorption at 1196 nm and 916 nm mainly correspond to the carbon-hydrogen vibrations of the $CH_3$ groups.

The normal paraffins may be expected to have a greater number of $CH_2$ groups than $CH_3$ groups relative to the other alkanes of the same carbon number which may be present in the kerosene. Consistent with this, we have found that the normal paraffins preferentially absorb light at 1210 nm and 927 nm relative to 1196 nm and 916 nm, respectively.

We have shown that the absorptivity in the above-mentioned wavelength ranges of kerosene can be used in a linear model to predict the wt % normal paraffin content. Only one wavelength need be used from these ranges to predict the normal paraffin content, however, greater accuracy is obtained using the difference between a pair of wavelengths as discussed in Example 1 below. For example, the difference in absorptivity at 1210 nm and 1196 nm can be used in a predictive model.

It is surprising, for several reasons, that the difference in absorptivity between one pair of wavelengths would contain sufficient information to predict the normal paraffin content of kerosene with sufficient accuracy. Firstly, there is an unknown and variable distribution of normal paraffins in kerosene, with the number of carbon atoms ranging, approximately, from 9 to 18. This distribution may vary with feed. In addition, the absorption spectrum of each of the individual normal paraffins are not identical but vary in amplitude, and spectral features. Furthermore, hydrocarbon molecules other than the normal paraffins also absorb in the same spectral region.

The spectra of the kerosene, sievate, and desorbate appear quite similar, with broad, overlapping, and unresolved features. While it might be expected that a predictive model could be constructed using the absorbance at many wavelengths, it is certainly not obvious that a two wavelength model could predict the normal paraffin content to within 1 wt %.

Means to determine the absorptivity difference may be much less expensive relative to means for obtaining an entire spectrum comprising the absorptivity at many wavelengths.

EXAMPLE 1

Determination of the Normal Paraffin Content of Kerosene Feeds

The absorption spectra of 36 plant samples of kerosene feeds, having normal paraffin content ranging from 12.88 wt % to 18.1 wt % as determined by gas chromatography (GC), were recorded between 800 nm and 1600 nm at 1 nm intervals. The samples were measured, without dilution, in optical path lengths of 5 cm and 1 cm, for the 800 nm to 1000 nm and the 1000 nm to 1600 nm ranges, respectively. Four consecutive 3 minute scans were averaged and stored for each sample.

FIG. 1 shows the absorption spectra for two kerosene feed samples having normal paraffin content of 14.7 wt % and 18.1 wt %. The spectra of 30 of the samples having intermediate normal paraffin content lie between these spectra. In order to minimize the effects of baseline drift and to maximize the sample-to-sample variance due to the preferential absorption by the normal paraffins of 1210 nm and 927 nm light, the absorbance, $A(1196)$, at 1196 nm, was subtracted from the absorbance, $A(1210)$, at 1210 nm, for each sample.

Figure 2:
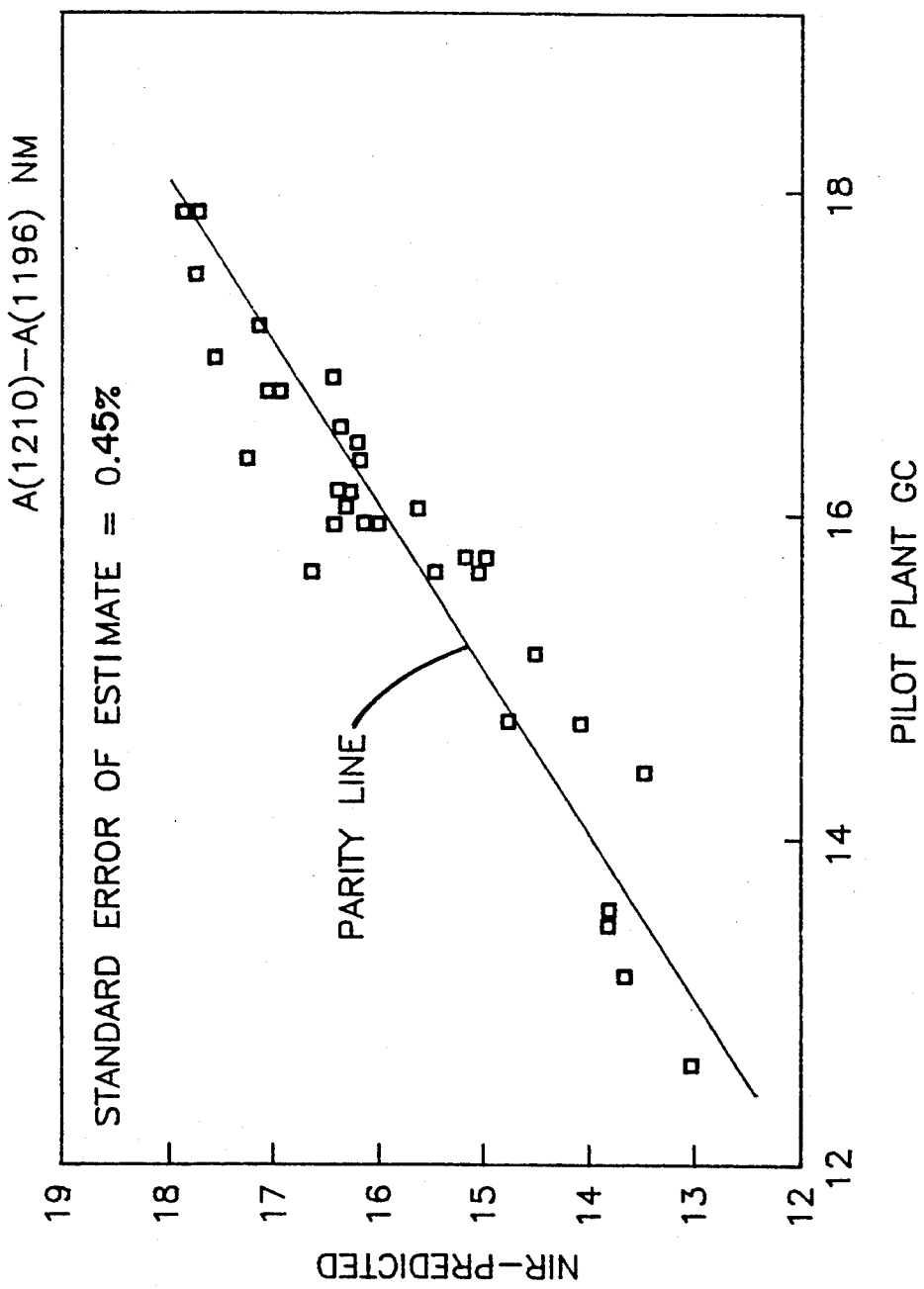
FIG. 2 shows a parity plot of the wt % normal paraffins kerosene as determined by gas chromatography versus estimated wt % as estimated from the difference in the near-infrared absorptivity at wavelengths 1210 nm and 1196 nm, for 30 samples.

The absorbance difference, $[A(1210)-A(1196)]$, was regressed using a least squares method against the normal paraffin content, as determined by GC, for the 36 feeds. The regression coefficients were used to estimate the normal paraffin content from the spectra. A standard error of estimate of 0.45 wt % was obtained for these samples. A parity plot of the GC versus spectrally-estimated results are shown in FIG. 2.

Figure 3:
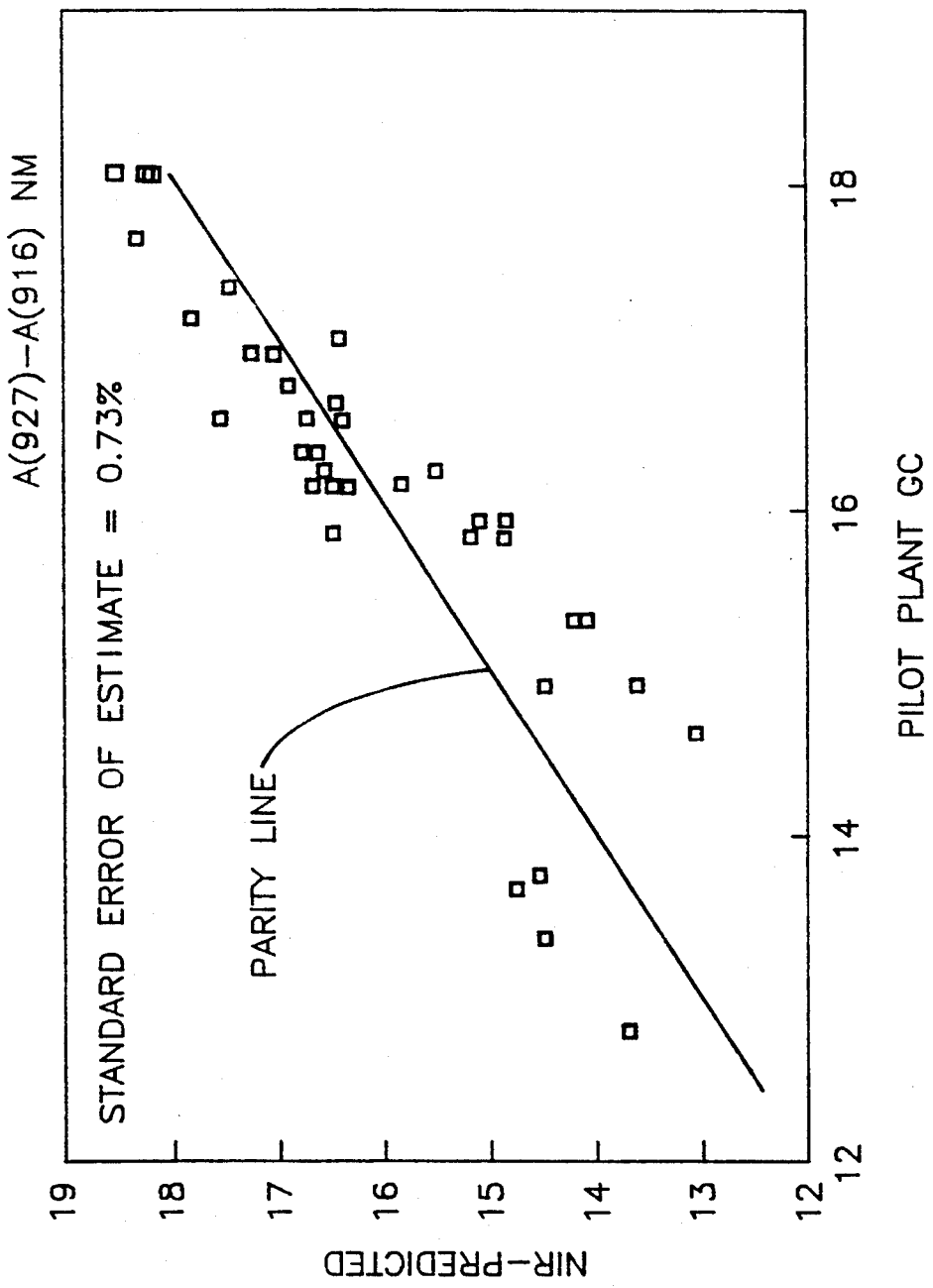
FIG. 3 shows a parity plot of the wt % normal paraffins in kerosene as determined by gas chromatography versus the wt % as estimated from the difference in the near-infrared absorptivity at wavelengths 927 nm and 916 nm, for 30 samples.

Similarly, the absorbance difference, $[A(927)-A(916)]$, was regressed against the normal paraffin content for the 36 feeds. A standard error of estimate of 0.73 wt % was obtained. A parity plot of the GC versus the spectrally-estimated results is shown in FIG. 3.

In the above examples, the differences in absorbance, rather than absorptivity was used, the absorptivity being defined as the absorbance per unit pathlength. Since the same pathlength was used for each of the two wavelengths in a given spectral region, the use of absorbance rather than absorptivity differences in the regression model, results in different regression coefficients. The estimated wt % normal paraffin values, however, remain unchanged. Also, the negative of the absorbance differences discussed in the previous two paragraphs may also be linearly related to the wt % normal paraffins, the regression coefficients will of course be different.

EXAMPLE 2

Determination of the Normal Paraffin Content of Sievate

To demonstrate the determination of the percent n-paraffins in a commercial sievate from 0-100% n-paraffins, and to eliminate the problems mentioned earlier with the GC measurements, known blends of sievate, with essentially 0% n-paraffin content and desorbate, which is essentially 100% n-paraffins, were measured.

Figure 4:
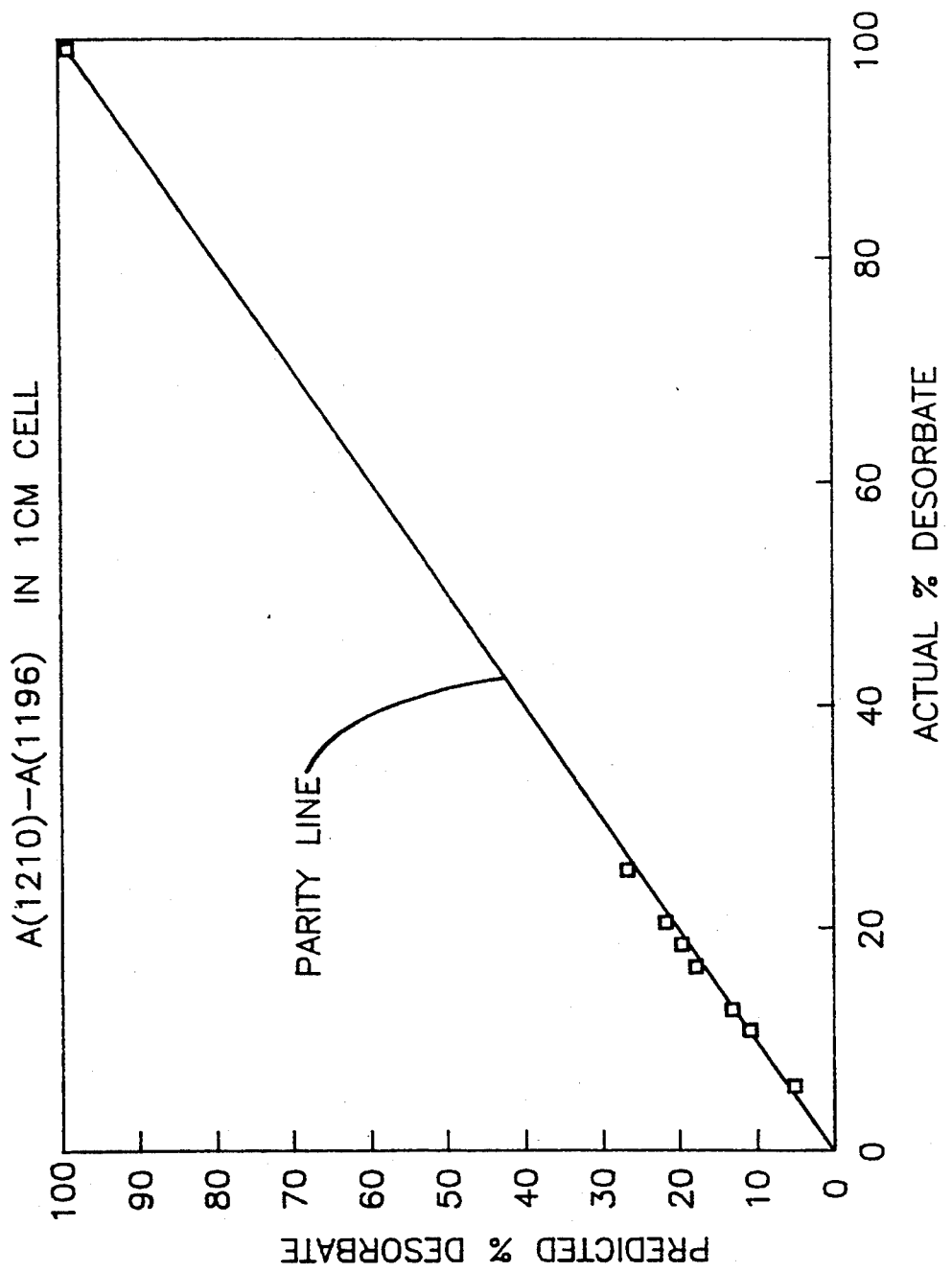
FIG. 4 is a parity plot of mixtures of sievate and several mixtures having different wt % desorbate, showing a comparison of the actual amount of desorbate and the amount of desorbate estimated from the difference in the near-IR absorptivity at wavelengths 1210 nm and 1196 nm.
Figure 5:
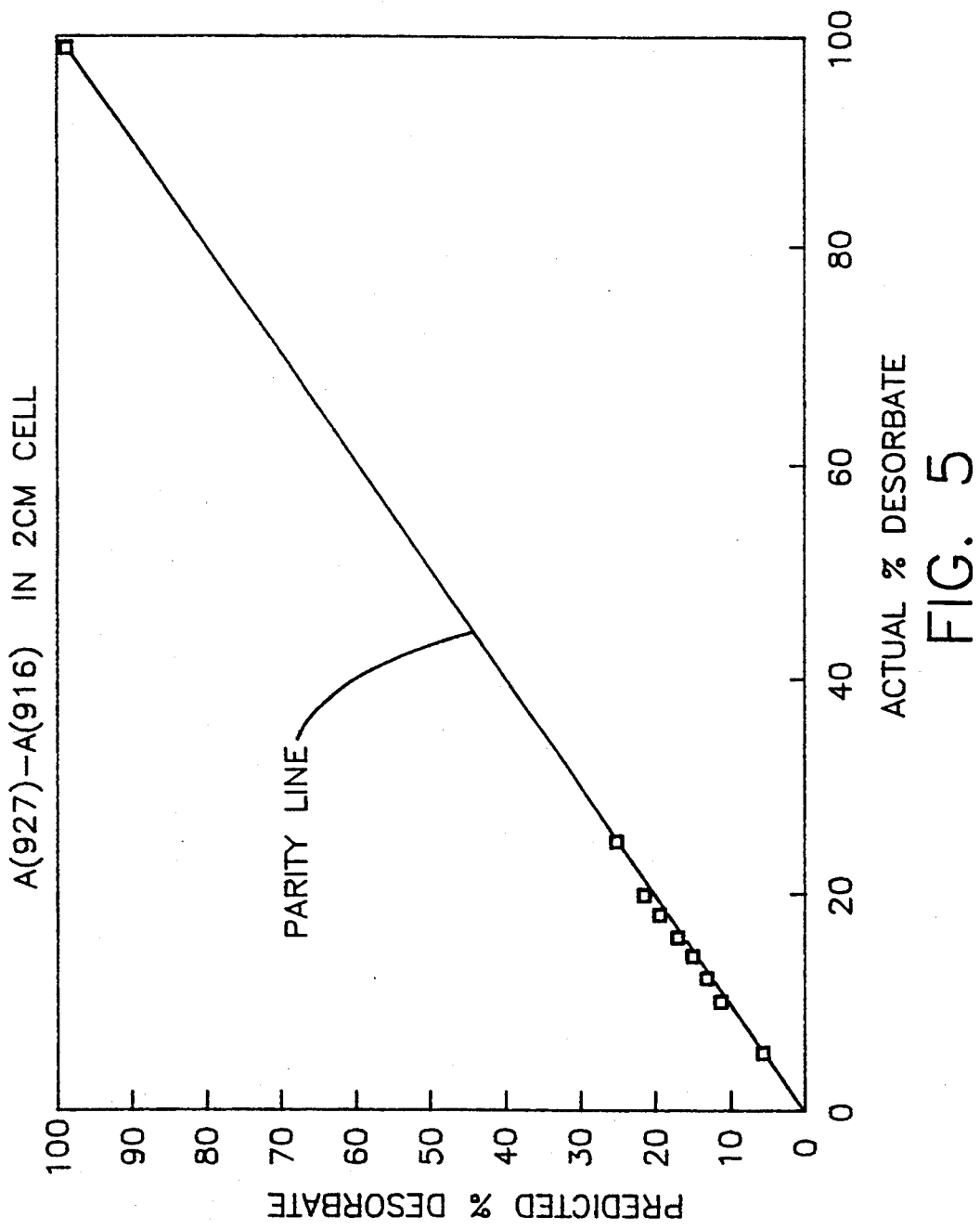
FIG. 5 shows a parity plot of mixtures of sievate and several mixtures having different wt % desorbate, showing a comparison of the actual amount of desorbate and the amount of desorbate estimated from the difference in the near-IR absorptivity at wavelengths 927 nm and 916 nm.

Mixtures of sievate and desorbate were prepared with 0, 5, 10, 12, 14, 16, 20, 25, and 100 wt % desorbate. The absorbance difference at both pairs of wavelengths, 1210 nm and 1196 nm and 927 nm and 916 nm, as described above, were correlated to the wt % desorbate in the mixture with a $R^2 > 0.999$. These data are shown in FIG. 4 and FIG. 5.

While the 1210 nm and 927 nm wavelengths have been chosen to provide information on the $CH_2$ vibrations, any wavelength or group of wavelengths in a band of approximately 10 nm or less can be used to provide correlation with normal paraffin content. While the 1196 nm and 916 nm wavelengths have been used as the second wavelength in the difference model, and are the preferred wavelengths, other wavelengths, such as 1100 nm, can be used.

The two wavelengths model can be implemented on-line using several hardware options. These range from relatively simple and low cost two-wavelength source/detector apparatus to full spectrometers. The light from both classes of device can be brought to and from the process line using fiber optics. The model involving the 900 nm band permits fiber optic techniques as well as low cost silicon detectors to be employed including diode array or charge coupled detectors. The model involving the 1200 nm band also permits the use of fiber optic techniques but requires the use of near infrared detectors. However, the prediction error is lower for the 1200 nm band, as discussed earlier.

What is claimed is:

1. A method to optimize the separation of normal paraffins from a petroleum distillate which includes paraffins by passing said petroleum distillate through a selective absorber of paraffins comprising:
   (a) irradiating a petroleum distillate feed stream and/or sievate with near-infrared radiation;
   (b) determining the optical absorptivity of said feed stream and/or sievate for at least one selected wavelength;
   (c) determining the normal paraffin content in said feed stream and/or sievate from said optical absorptivity; and
   (d) changing the selective absorber when said normal paraffin content indicates said absorber is becoming saturated.

2. The method of claim 1 wherein said method includes determining the optical absorptivity at a second selected wavelength, and determining the difference in the optical absorptivity, between said two wavelengths.

3. The method of claim 2 wherein the two selected wavelengths are about 1210 nm and 1196 nm.

4. The method of claim 2 wherein the two selected wavelengths are about 927 nm and 916 nm.

5. The method of claim 2 wherein said selective absorber is a molecular sieve.

6. The method of claim 5 wherein said molecular sieve is a zeolite molecular sieve.

7. The method of claim 2 wherein said hydrocarbon feedstream is kerosene.

8. The method of claim 1 wherein said irradiating and determining steps are applied only to said feedstream.

9. The method of claim 1 wherein said irradiating and determining steps are applied only to said sievate.

10. The method for optimally removing normal paraffins from a kerosene feedstream comprising:
    (a) feeding said feedstream through a first absorber which continuously removes normal paraffins;
    (b) irradiating said feedstream and/or sievate emerging from said absorber with optical radiation of at least one wavelength;
    (c) determining the optical absorptivity of said feedstream and/or sievate,
    (d) determining the weight percent of said paraffins in said feedstream and/or sievate from said optical absorptivity; and
    (e) switching said feedstream to a second absorber when said weight percent shows that said first absorber is no longer removing paraffins from said feedstream.

11. The method of claim 10 wherein said method includes determining the optical absorptivity at a second selected wavelength, and determining the difference in the optical absorptivity, between said two wavelengths.

12. The method of claim 11 wherein the two selected wavelengths are about 1210 nm and 1196 nm.

13. The method of claim 11 wherein the two selected wavelengths are about 927 nm and 916 nm.

14. The method of claim 10 wherein each absorber is a molecular sieve.

15. The method of claim 14 wherein each molecular sieve is a zeolite molecular sieve.

16. The method of claim 10 wherein said irradiating and determining steps are applied only to said feedstream.

17. The method of claim 10 wherein said irradiating and determining steps are applied only to said sievate.

* * * * *